(12) United States Patent
Amari et al.

(10) Patent No.: US 7,736,662 B2
(45) Date of Patent: Jun. 15, 2010

(54) NATURAL EMULSIFIER FOR COSMETICS BASED ON OLIVE OIL

(75) Inventors: Sergio Amari, Paderno d'Adda (IT); Cristina Schubert, Milan (IT)

(73) Assignee: B&T S.R.L., Milan (IT)

( * ) Notice: Subject to any disclaimer, the term of this patent is extended or adjusted under 35 U.S.C. 154(b) by 0 days.

(21) Appl. No.: 10/466,909

(22) PCT Filed: Oct. 16, 2002

(86) PCT No.: PCT/IB02/04233

§ 371 (c)(1), (2), (4) Date: Jul. 23, 2003

(87) PCT Pub. No.: WO03/032943

PCT Pub. Date: Apr. 24, 2003

(65) Prior Publication Data

US 2004/0156817 A1    Aug. 12, 2004

(30) Foreign Application Priority Data

Oct. 16, 2001    (IT)    .......................... MI2001A2139

(51) Int. Cl.
*A61K 8/02* (2006.01)
*A01N 25/00* (2006.01)

(52) U.S. Cl. ...................... 424/401; 514/772

(58) Field of Classification Search ........................ None
See application file for complete search history.

(56) References Cited

U.S. PATENT DOCUMENTS

| 2,333,093 | A | * | 11/1943 | Dearborn | 514/430 |
| 3,288,824 | A | | 11/1966 | Gattefosse et al. | |
| 5,527,523 | A | * | 6/1996 | Laruelle et al. | 424/62 |
| 5,770,185 | A | * | 6/1998 | Wachter et al. | 424/65 |
| 6,017,549 | A | * | 1/2000 | Knight et al. | 424/401 |
| 6,140,435 | A | * | 10/2000 | Zanotti-Russo | 526/238.2 |
| 6,488,946 | B1 | * | 12/2002 | Milius et al. | 424/401 |
| 6,500,440 | B1 | * | 12/2002 | Chi et al. | 424/401 |
| 2001/0006665 | A1 | | 7/2001 | Auguste | |

FOREIGN PATENT DOCUMENTS

| DE | 43 38 591 | | 5/1995 |
| EP | 0 589 843 | | 3/1994 |
| GB | 450 368 | | 7/1936 |
| WO | WO 99/29814 A2 | * | 6/1999 |

OTHER PUBLICATIONS

Rigano et al. (Olivem 900: Make up e skin care. Cosmetic News 1999; XXII (126): 211-5).*
Database WPI, Section Ch, Week 200168 Derwent Publications Ltd., London, GB, AN 2001-600663, XP002231217 & KR 2001 038 071 A (Pacific Ind Co), May 15, 2001 abstract.
Database CA 'Online! Chemical Abstracts Service, Columbus, Ohio, US; Arcos, Jose A et al: "Quantitative enzymic production of 1,6-diacly sorbitol esters" retrieved from STN Database accession No. 129:274734 XP002231216 Abstract -& Biotechnology and Bioengineering (1998), 60(1), 53-60, XP002231214.
Coternon A., et al.:, "Reactions of Olive Oil and Glycerol over Immobilized Lipases", JAOCS, vol. 75, No. 5, 1998, pp. 657-660, XP001135083, experimental procedures p. 658.
Umbach W.:, "Kosmetik: Entwicklung, Herstellung und Anwendung kosmetischer Mittel", 1988, Georg Thieme Verlag, Stuttgart XP002231215, p. 510, paragraph 2 -p. 511, paragraph 2.
Quantitative Enzymatic Production of 1,6-Diacyl Sorbitol Esters, Jose A. Arcos et al.:, XP-002231214, p. 53-60.

* cited by examiner

*Primary Examiner*—Sreeni Padmanabhan
*Assistant Examiner*—Layla Soroush
(74) *Attorney, Agent, or Firm*—Kenyon & Kenyon LLP

(57) ABSTRACT

The present invention relates to a natural ethylene oxide-free emulsifier composed of olive oil, the fatty acid of which have been esterified, preferably with sorbitol and/or cetyl stearyl alcohol. The present invention also relates to cosmetics containing, as an emulsifier, an emulsifier as described above, as well as a method for manufacturing such a product for cosmetic use.

23 Claims, No Drawings

NATURAL EMULSIFIER FOR COSMETICS BASED ON OLIVE OIL

The present invention relates to a natural emulsifier for cosmetics, in particular an emulsifier free from ethylene oxide and derivatives thereof.

In the cosmetics field, it is necessary to be able to emulsify lipid phases with aqueous phases, so as to obtain stable products, which do not incur into unmixing during the normal use of said product. In order to achieve such an object, an emulsifier is usually added to said products, enabling to. keep the emulsions to which it is added stable. One of the main problems is that the emulsifier should not impart its own characteristics to the finished product, as they may impair the quality or the action of the product, or make the product look or smell unpleasant.

As emulsifiers, derivatives of ethylene oxide are often used, which work quite well, but tend to form free radicals, which have the unwanted effect of favouring skin ageing.

These problems and drawbacks are brilliantly solved by the present invention, relating to a natural ethylene oxide-free emulsifier, characterized in that it is made of olive oil, the fatty acids of which have been esterified.

Preferably, the esterification of the fatty acids is done with sorbitol and/or cetyl stearyl alcohol.

The present invention also relates to cosmetic products, in particular soaps, liquid soaps, special soaps, creams, sticks, make-up products, shampoos and lipsticks or the like, containing the above emulsifier.

The emulsifier according to the present invention is manufactured from pure olive oil, undergoing esterification with sorbitol and/or cetyl stearyl alcohol. The esterification is performed according to the methods known in organic chemistry. A self-emulsifying product is therefore obtained. This product-once into an emulsion-forms liquid crystals allowing to obtain stable products, as desired. Of course, the present invention also extends to emulsifiers obtained by mixing the individual esters of the olive oil acids, each taken separately. The emulsifier obtained according to the present invention confers a silky texture. The natural origin of the product also provides a relevant hydrating effect and good smoothness. The gel lattice that is formed allows the product to quickly penetrate into the skin and to reduce the loss of skin moisture, with a strongly desirable hydrating effect.

The liquid crystals that are formed orientate so as to place their polar heads towards the aqueous phase and their apolar tails towards the lipid phase. In this way, a multi-layer lamellae structure forms, which confers high stability to the product, apart from significant brightness and a shiny appearance.

By using the emulsifier according to the present invention, it is possible to introduce high concentrations of lipids, up to 30% at least.

Cosmetics according to the present invention usually contain up to 10% emulsifier, preferably between 0,5% and 8%. Cosmetics containing up to 10% emulsifier and hydrogenated lecithin or lecithin derivatives are particularly valuable.

The cosmetic products according to the present invention may be prepared according to the following steps:
a) melting the lipid phase at 70°-75° C.;
b) mixing the aqueous phase and heating it to 70° C.;
c) while homogenising, trickle-feeding the lipid phase directly into the aqueous phase;
d) homogenising for 5-10 minutes;
e) cooling under stirring.

The stirring speed determines the viscosity of the finished product, a lower speed resulting in a lower viscosity. The ideal stirring is obtained, for a 500 cm$^3$ container, within a 500 to 5000 revolutions/minute range, preferably at 2000 revolutions/minute, or in equivalent conditions.

If the emulsifier concentration of the product is 2-3%, step c) may be replaced by the following step:
c1) while homogenising, trickle-feeding the aqueous phase directly into the lipid phase.

The present invention is hereafter illustrated more in depth, on the basis of the following formulation examples. The indicated percentages (expressing weight) refer to the whole of the finished product, while other cosmetic bases are cited with their commercial names.

FORMULATION EXAMPLE 1

The aqueous phase was composed of 0,1% Carbopol 2050 and deionised water for balance. The lipid phase was composed of 6% emulsifier according to the present invention, 5% alkylbenzoate C12-C15, 5% sweet almond oil, 10% sesame oil and 5% mineral oil. To the product obtained according to the method illustrated in the text, sodium hydroxide, perfume and preservatives were added in the required quantities. A nourishing cream was thus obtained.

FORMULATION EXAMPLE 2

The lipid phase was composed of 2% emulsifier according to the present invention, 5% isononyl isononanoate, 10% wheat germ oil, 0.5% dimethicone and 0.5% hydrogenated lecithin. The aqueous phase was composed of 0,4% xanthan gum and deionised water for balance. To the product obtained as described above, 0.1% olive tree leaves extract and preservatives were added in the required quantities. A hydrating lotion was thus obtained.

FORMULATION EXAMPLE 3

The lipid phase contained 3% emulsifier according to the present invention, 2% Olivem 700, 10% caprylicicapric triglyceride, 5% isononyl isononanoate, 0.5% benzophenone 3, 5% ethylhexyl methoxycinnamate, 2% titanium dioxide and 0.5% hydrogenated lecithin. The aqueous phase was composed of 1.2% xanthan/bentonite gum, 0.2% polyether-1 and deionised water for balance. To the product obtained according to the method as described above, preservatives and perfumes in the required quantities and 0.2% olive tree leaves extract were added. A sun cream with theoretical protection factor of 8 was obtained.

FORMULATION EXAMPLE 4

The lipid phase was composed of 8% emulsifier according to the present invention. The aqueous phase was composed of deionised water. To the product obtained as above, 2.5% cetrimonium chloride and perfumes and preservatives in the required quantities were added. A hair mask was obtained.

FORMULATION EXAMPLE 5

The lipid phase was composed of 2% emulsifier according to the invention, 7% isopropyl myristate, 2% sunflower oil, 2% cetyl alcohol.

The aqueous phase comprised 0.7% Carbopol Ultrez 10, 2% propylene glycol, 0.3% Pemulen TR1 and deionised water for balance. 7% Plantacare 2000, 15% Olivem 400 and 1% Olivem 300 were further added to the product obtained; in addition, perfumes and preservatives in the required quantities were added and the pH was adjusted to 6.3 (with a 0.5 deviation) with sodium hydroxide. A cleansing cream was thus obtained.

FORMULATION EXAMPLE 6

The aqueous phase comprised deionised water and 1.5% emulsifier according to the invention.

The lipid phase was composed of 10% Plantacare 2000, 12% Olivem 400, 10% Tegobetaine HS60, 2% Amphotesid B5.

To the product, obtained as above, 2% Glucquat C125 was added. A shampoo was obtained.

FORMULATION EXAMPLE 7

The aqueous phase contained deionised water, 3% glycerine and 2.5% emulsifier according to the invention.

The lipid phase contained 2% Olivem 300, 12% Olivem 400, 20% Sles (28% salified) 2% Cocamide Dea and 5% cocamidopropyl betaine.

After the aqueous dispersion was formed, the lipid phase was slowly added to the aqueous phase under stirring, with neutralisation of the final solution. Sodium hydroxide was then added, up to a pH 6 (with a 0.5% variation), then 0.1% olive tree leaves extract, perfumes, and preservatives were added in sufficient quantity. A bath foam was obtained.

FORMULATION EXAMPLE 8

The lipid phase contained 3% emulsifier according to the present invention, 2% mineral oil, 10% isopropyl myristate, 2% cyclomethicone and 3% caprylic/capric trygliceride.

The aqueous phase comprised deionised water, 0.3% Carbopol Ultrez, 3% diglycerine and 0.1% powdered aloe.

The two phases were separately heated to 70°-75° C., the lipid phase was then added to the aqueous phase, homogenising for 5 minutes. Subsequently, it was cooled under stirring and the pH was brought to 6 (0.5% variation) with sodium hydroxide. After adding perfume, a day cream was obtained.

FORMULATION EXAMPLE 9

The lipid phase comprised 3% emulsifier according to the invention, 2% Olivem 300, 0.5% hydrogenated lecithin, 5% disodecyl neopentanoate, 5% propylene glycol dicaprate, 4% triundecanoine, 5% caprylic/capric triglyceride and 5% squalane.

The aqueous phase contained water, 5% glycerine, 0.4% xanthan gum, 0.6% magnesium and aluminium silicate. The two phases were separately heated to 70° C. Subsequently, 3% talc, 0.3% Cl 77499, 0.4% Cl 77491/2/9, 4.8% Cl 77891, 1.5% Cl 77492 and perfumes and preservatives were dispersed in the aqueous phase in the necessary quantity,. under stirring. The lipid phase was then added to the product under stirring. A foundation cream was obtained.

FORMULATION EXAMPLE 10

The lipid phase contained 5% emulsifier according to the invention, 2% Olivem 300, 5% caprylic/capric triglyceride, 10% dimethicone and 5% squalane.

The aqueous phase contained water, 5% glycerine, 0.4% xanthan gum, 0.6% magnesium and aluminium silicate and 1.5% polyvinylpyrrolidone.

The phases were separately heated to 70° C. In the aqueous phase, 3% talc and 10% Cl 77499 were dispersed. Subsequently, the lipid phase was added to the mixture obtained under stirring. After cooling it under stirring, perfumes and preservatives were added. A Mascara was obtained.

FORMULATION EXAMPLE 11

The aqueous phase comprised deionised water and 2% magnesium sulphate.

The lipid phase contained 5% cyclomethicone and dimethiconol, 10% cyclomethicone and dimethicone copolyol, 2% emulsifier according to the invention, 8% cyclomethicone, 10% titanium dioxide and ethylhexyl methoxycinnamate for balance.

The lipid phase was very slowly added to the aqueous phase under stirring, in order to obtain a sun cream with protection factor between 20 and 25.

The invention claimed is:

1. A method for manufacturing a cosmetic composition containing an emulsifier comprising:
   providing a lipid phase having an emulsifier comprising olive oil that has undergone esterification with sorbitol and cetyl stearyl alcohol;
   melting the lipid phase at 70°-75° C.;
   providing an aqueous phase and heating the aqueous phase;
   homogenizing the lipid phase and the aqueous phase by trickle-feeding the lipid phase into the aqueous phase;
   homogenizing for 5-10 minutes; and
   cooling while stirring;
   wherein said emulsifier comprising olive oil that has undergone esterification with sorbitol and cetyl stearyl alcohol is free of ethylene oxide and forms liquid crystals.

2. The method as in claim 1, wherein said stirring is performed within a 500 to 5000 revolutions/minute range.

3. The method according to claim 1, wherein the aqueous phase is heated to 70° C.

4. A topical composition comprising:
   a lipid component;
   an aqueous component; and
   an emulsifier comprising olive oil that has undergone esterification with sorbitol and/ cetyl stearyl alcohol,
   wherein said emulsifier comprising olive oil that has undergone esterification with sorbitol and cetyl stearyl alcohol is free of ethylene oxide and the composition forms a stable oil-in-water emulsion.

5. The composition of claim 4, wherein the emulsifier is present in an amount of 0.5 to 8 wt% of the composition.

6. The composition of claim 4, wherein the lipid component is in an amount of at least 30 wt%.

7. The composition of claim 4, wherein the composition is in a form selected from the group consisting of soaps, liquid soaps, creams, sticks, make-up products, shampoos, lotions, bath foams, hair masks, and lipsticks.

8. A topical composition comprising:
   a lipid component;
   an aqueous component; and
   an emulsifier comprising olive oil that has undergone esterification with sorbitol and/ cetyl stearyl alcohol,
   wherein said emulsifier comprising olive oil that has undergone esterification with sorbitol and cetyl stearyl alcohol is free of ethylene oxide and the composition forms a stable emulsion having a multi-layer lamellar structure.

9. A topical composition in the form of an emulsion comprising esterified olive oil as the emulsifier, wherein esterification agent comprises sorbitol and cetyl stearyl alcohol and the esterified olive oil is free of ethylene oxide wherein once in the emulsion, the emulsifier forms liquid crystals comprising polar heads and apolar tails which orientate so that the polar heads are placed toward an aqueous phase and the apolar tails are placed towards a lipid phase.

10. The topical composition according to claim 9, wherein the amount of emulsifier is 10 % or less.

11. The topical composition according to claim 4, further comprising hydrogenated lecithin.

12. The topical composition according to claim 4, wherein the amount of emulsifier is 10 % or less by weight.

13. A process of manufacturing a topical composition containing an emulsifier comprising adding the emulsifier in an aqueous or a lipid phase and mixing the aqueous phase with the lipid phase to form a stable emulsion, wherein the emulsifier comprises olive oil which has undergone esterification with sorbitol and cetyl stearyl alcohol and the emulsion is in the form of a topical composition, and wherein said emulsifier comprising olive oil that has undergone esterification with sorbitol and cetyl stearyl alcohol is free of ethylene oxide.

14. A process of manufacturing a topical composition containing an emulsifier according to claim 13, comprising adding the emulsifier in an aqueous or a lipid phase and mixing the aqueous phase with the lipid phase to form a stable emulsion.

15. A composition comprising a liquid phase, an aqueous phase and an emulsifier wherein the emulsifier comprises olive oil which has undergone esterification with sorbitol and cetyl stearyl alcohol, wherein said emulsifier comprising olive oil that has undergone esterification with sorbitol and cetyl stearyl alcohol is free of ethylene oxide said composition being in the form of a cosmetic product.

16. The composition of claim 15, wherein the cosmetic product is selected from the group consisting of soaps, liquid soaps, creams, sticks, make-up products, shampoos, lotions, bath foams, hair masks, and lipsticks.

17. An emulsifying agent comprising olive oil that has been esterified with sorbitol and cetyl stearyl alcohol wherein the emulsifying agent is free of ethylene oxide.

18. A topical composition comprising the emulsifying agent of claim 17.

19. The topical composition of claim 18, wherein the composition is in a form selected from the group consisting of soaps, liquid soaps, creams, sticks, make-up products, shampoos, lotions, bath foams, hair masks, and lipsticks.

20. The process of claim 14, wherein the composition is in a form selected from the group consisting of soaps, liquid soaps, creams, sticks, make-up products, shampoos, lotions, bath foams, hair masks, and lipsticks.

21. The process of claim 14, wherein the composition is a cream or lotion.

22. The composition of claim 15, wherein the composition is in a form selected from the group consisting of soaps, liquid soaps, creams, sticks, make-up products, shampoos, lotions, bath foams, hair masks, and lipsticks.

23. The process of claim 15, wherein the composition is a cream or lotion.

* * * * *

UNITED STATES PATENT AND TRADEMARK OFFICE
CERTIFICATE OF CORRECTION

| | |
|---|---|
| PATENT NO. | : 7,736,662 B2 |
| APPLICATION NO. | : 10/466909 |
| DATED | : June 15, 2010 |
| INVENTOR(S) | : Sergio Amari et al. |

It is certified that error appears in the above-identified patent and that said Letters Patent is hereby corrected as shown below:

Column 1, line 54, change "0,5%" to -- 0.5% --;

Column 2, line 15, change "0,1%" to -- 0.1% --;

Column 2, line 29, change "0,4%" to -- 0.4% --;

Column 3, line 54, change "quantity,." to -- quantity, --;

Column 5, line 24, change "liquid phase" to -- lipid phase --.

Signed and Sealed this

Seventeenth Day of August, 2010

David J. Kappos
*Director of the United States Patent and Trademark Office*